United States Patent
Jattke et al.

(10) Patent No.: US 8,314,617 B2
(45) Date of Patent: Nov. 20, 2012

(54) METHOD FOR AT LEAST PARTLY DETERMINING AND/OR ADAPTING AN ATTENUATION MAP USED FOR CORRECTING ATTENUATION OF POSITRON EMISSION TOMOGRAPHY IMAGE DATA SETS IN A COMBINED MAGNETIC RESONANCE-POSITRON EMISSION TOMOGRAPHY DEVICE

(75) Inventors: Kirstin Jattke, Nürnburg (DE); Ralf Ladebeck, Erlangen (DE); Christian J. Michel, Lenoir City, TN (US); Thorsten Speckner, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 548 days.

(21) Appl. No.: 12/585,539

(22) Filed: Sep. 17, 2009

(65) Prior Publication Data

US 2010/0066385 A1    Mar. 18, 2010

(30) Foreign Application Priority Data

Sep. 18, 2008 (DE) .......................... 10 2008 047 840

(51) Int. Cl.
*G01V 3/00* (2006.01)
(52) U.S. Cl. ........................................ 324/309; 324/307
(58) Field of Classification Search .................. 324/307, 324/309, 312, 314
See application file for complete search history.

(56) References Cited

U.S. PATENT DOCUMENTS

| | | | |
|---|---|---|---|
| 7,869,860 B2 * | 1/2011 | Kinahan et al. | 600/425 |
| 7,888,632 B2 * | 2/2011 | Ladebeck et al. | 250/252.1 |
| 2008/0135769 A1 * | 6/2008 | Rosen | 250/363.09 |
| 2010/0021034 A1 * | 1/2010 | Lenglet et al. | 382/131 |
| 2011/0158497 A1 * | 6/2011 | Schweizer et al. | 382/131 |
| 2011/0164801 A1 * | 7/2011 | Gagnon et al. | 382/131 |
| 2011/0172517 A1 * | 7/2011 | Schmidt | 600/411 |

FOREIGN PATENT DOCUMENTS

| | | |
|---|---|---|
| DE | 102007011695 A1 | 9/2008 |
| WO | WO 9705574 A1 | 2/1997 |

OTHER PUBLICATIONS

German Office Action dated Dec. 16, 2009.

* cited by examiner

*Primary Examiner* — Louis Arana
(74) *Attorney, Agent, or Firm* — Harness, Dickey & Pierce, P.L.C.

(57) ABSTRACT

A method is disclosed for at least partly determining and/or adapting an attenuation map used for attenuation correction of Positron Emission Tomography image data sets in a combined Magnetic Resonance-Positron Emission Tomography device. In at least one embodiment of the method, at least one one-dimensional magnetic resonance data set of a patient is recorded along one imaging direction; the boundaries of at least one part of the body of the patient intersected by the imaging direction are determined from the one-dimensional magnetic resonance data set; and the attenuation map is determined and/or adapted at least partly as a function of the boundaries determined.

19 Claims, 5 Drawing Sheets

METHOD FOR AT LEAST PARTLY DETERMINING AND/OR ADAPTING AN ATTENUATION MAP USED FOR CORRECTING ATTENUATION OF POSITRON EMISSION TOMOGRAPHY IMAGE DATA SETS IN A COMBINED MAGNETIC RESONANCE-POSITRON EMISSION TOMOGRAPHY DEVICE

PRIORITY STATEMENT

The present application hereby claims priority under 35 U.S.C. §119 on German patent application number DE 10 2008 047 840.7 filed Sep. 18, 2008, the entire contents of which are hereby incorporated herein by reference.

FIELD

At least one embodiment of the invention generally relates to a method for at least partly determining and/or adapting an attenuation map used for correcting attenuation of Positron Emission Tomography image data sets in a combined Magnetic Resonance-Positron Emission Tomography device.

BACKGROUND

In Positron Emission Tomography (PET), the emitted photons are attenuated during their passage through the object to be imaged, especially the human body. Thus artifacts occur in reconstructed PET images as well as limitations in the quantitative evaluation. To rectify this problem it is known that an attenuation correction based on an attenuation map can be carried out. In the final analysis the attenuation map specifies how large the local attenuation coefficient is at specific positions within the body. For the attenuation correction it is necessary for the exact position and density of the body parts and anatomical structures of an object under examination to be determined. For stand-alone PET systems the attenuation map can be determined for example from CT images or from external sources.

In recent times however hybrid magnetic resonance PET devices (MR-PET devices) have been developed which ideally allow parallel imaging based on MR and PET. In these devices techniques have been proposed for also using MR imaging to determine the position of anatomical features or even the tissue distribution. Furthermore it has been proposed that an attenuation map determined previously with another device also be used for MR.

In such cases however it is precisely with hybrid MR-PET devices that difficulties arise. On the one hand an MR-PET device mostly provides only a very restricted patient image, meaning an image with a small radius in which, in particular as regards the extremities, mainly the arms, patients position themselves differently. An exact, reliable and diagnostically-evaluatable MR image is in addition only possible in a restricted area in which the field exhibits a sufficient homogeneity and the gradient fields a sufficient linearity. This area frequently lies in the area of the torso. Images of the arms or if necessary also of the legs, which are located at the edge of the patient image, with diagnostic quality are thus not possible. In particular the non-linearity of the gradient fields results in distortions, but image artifacts can also arise from the lack of homogeneity. Thus there has not been any method known to date of reliably recording images in a combined MR-PET device of the position of parts of the body of a patient, and also it is only possible with difficulty—especially in the area of the arms—to obtain information needed to adapt or to determine an attenuation map.

SUMMARY

In at least one embodiment of the present invention, a method is specified with which an adaptation and/or determination of the attenuation map is made possible even in areas situated far away from the field of view for magnetic resonance.

To resolve this problem, at least one embodiment of the invention provides, in a method, for
at least one one-dimensional magnetic resonance data set of a patient to be recorded along a direction of imaging,
from the one-dimensional magnetic resonance data set the boundaries of a least one part of the body of the patient intersected by the imaging direction to be determined,
the attenuation map to be determined and/or adapted at least partly as a function of the boundaries determined.

It is thus proposed that a one-dimensional imaging technique be used in order to obtain the projection of the anatomy of a patient on one axis, typically a left-to-right axis. These one-dimensional image recording techniques have a whole series of advantages. First of all they can be executed extremely quickly, especially in the range of just a few milliseconds. In this way the position of parts of the body, especially of the arms, can be measured quickly, i.e. without imposing any strain on the patient by making them stay too long in the combined MR-PET device. At the same time the projection on only a single axis compensates for the distortions and artifacts lying outside the field of view of the magnetic resonance device.

In such cases it has been recognized within the context of at least one embodiment of the present invention that, although it is not possible to obtain images of diagnostic quality outside the field of view, the one-dimensional magnetic resonance data sets still allow a sufficiently exact determination of the position and if necessary can even give information for estimating the attenuation coefficient. Steep signal edges in such cases give indications of the position of different parts of the body, and in some embodiments of the present invention the signal level can additionally be used to adapt and or to determine at least one part of the attenuation map.

As described, the attenuation map can be at least partly determined and/or adapted. It is thus basically possible with at least one embodiment of the inventive method both to further evaluate a prefabricated attenuation map, for example from a model or from preceding examinations of the patient, from CT examinations for example, to position it correctly or to scale it and to adapt it and/or to supplement it at the appropriate points. It is also equally easily possible for example to determine a part of the attenuation map by dedicated magnetic resonance imaging in the area of the torso for example, in order thereafter, because of the one-dimensional measurement, to accordingly expand this attenuation map, by adapting a model for the body parts in the area of the imaged body parts, especially of the arms.

In this case there can be provision in a concrete embodiment of a sequence for recording a one-dimensional magnetic resonance data set along one direction of imaging, for a frequency with local encoding to be used for recording the magnetic resonance data set during the imaging solely in the imaging direction. This means that gradients for local encoding are switched after layer selection during excitation not in two spatial directions as is usual, but only in one, namely the imaging direction. This means that all signals of a direction perpendicular to the imaging direction will be measured simultaneously at the different points of the imaging direction, so that a type of projection is produced.

A spin echo sequence can be used to record the magnetic resonance data set. This has proved to be particularly advantageous in trials relating to at least one embodiment of the present invention for achieving sufficient contrast.

One problem in the recording of one-dimensional magnetic resonance data sets is what is known as phase dispersion. As a result of the characteristics of the material of the body to be imaged it can occur that other phases are present in different areas. If the phase difference between these areas even amounts to 180°, the result can be extinction of signals. Especially frequently such a condition is observed in areas of the torso since greatly differing material properties are present in different areas there and, since a projection will eventually be measured, all these areas perpendicular to the imaging direction contribute to the overall signal or can even attenuate the latter.

Thus it can be particularly advantageous for there to be provision, for recording the magnetic resonance data set, for a layer selection to be undertaken in two directions perpendicular to one another and to the direction of imaging, so that an essentially rectangular area is measured out in one dimension. Such a technique can be referred to as the pencil beam technique.

Instead of only one layer, for example in the cranial-caudial direction, being selected, a further layer is selected within the framework of the sequence, in the anterior-posterior direction for example, so that the area lying perpendicular to the direction of imaging which will eventually be projected onto the imaging axis, is reduced. This means that phase dispersion affects play a far smaller role and instead signals that can be evaluated are generated.

In a first embodiment of the invention there can actually be provision in such cases for a sequence with two excitation pulses to be used, in which a layer selection gradient is switched in each case in two directions perpendicular to each other and to the imaging direction. In such cases two excitation pulses are thus used which both take effect only in the recently imaged area with an essentially rectangular cross section.

In a second especially useful embodiment there can be provision, when a spin echo sequence is used, for a layer selection gradient to be switched for the refocusing pulse which is perpendicular to the direction selected for the layer selection gradient with the excitation pulse and to the direction of imaging. With a spin echo sequence a refocusing pulse, especially a 180° pulse is usually used. If this refocusing pulse is now restricted in its area of activity in a direction perpendicular to the actual layer selection for the excitation pulse and the imaging direction, an area essentially rectangular in cross section is selected in an elegant manner.

For the imaging of the magnetic resonance data set a sequence highlighting at least one type of tissue can be used, especially a T1 or T2-weighted sequence and/or a water or fat-suppressing sequence. In this case the sequence type to be selected in the final analysis is that which generates the one-dimensional magnetic resonance data sets which can be best evaluated. There can however also be provision for undertaking a number of consecutive measurements for example with different sequences and deriving further information from the differences between the individual magnetic resonance data sets, which for example allows a better determination and/or adaptation of the attenuation map. It is thus known for example that in water-suppressing sequences fatty tissue tends to be highlighted, in fat-suppressing sequences it is the watery muscle tissue instead. Thus for example the quantity of fatty or watery tissue can be determined in the direction of imaging.

It is thus basically possible in accordance with at least one embodiment of the invention for a number of different magnetic resonance data sets to be recorded for example 2 to 6, especially 3. As shown above, this is to be understood on the one hand as one-dimensional magnetic resonance data sets being recorded with different sequences, but in the same area, on the other hand it is naturally sensible to measure the position of parts of the body at a number of points along the patient. Thus for example, if the position of the arms is determined, three one-dimensional magnetic resonance data sets reflecting the progress in the right-to-left direction are recorded, approximately one in the area of the shoulders, one in the area of the upper arms and another in the area of the lower arms or hands. The course of the arms can then be extrapolated from this. Naturally however it is basically possible, depending on how accurate the information obtained is to be, in the final analysis to have any number of rapidly recorded one-dimensional measurements.

As already mentioned, to measure the position of the arms for example, there can be provision for the imaging direction to be a right-to-left direction and for a layer selection to be undertaken at the least in a cranial-caudal direction. To determine the position of the arms and if necessary of the torso of the patient there can also be provision for the or for one imaging direction to cut across the arms and the torso of the patient.

The measures by which the determination of the boundaries and thus of the position and extent of the parts of the body can be advantageously undertaken will now be explained below in greater detail.

There can thus be provision for an average noise value of a noise signal to be determined from the magnetic resonance data set or from a further data set especially recorded without a patient, with the exceeding of a first threshold value depending on the average noise value, especially five times the average noise value being used by the measurement signal starting from a noise signal range to determine a boundary. Accordingly the knowledge is used that—for example in the case of the arms, there is nothing else outside the outermost part of the body for which the boundaries are to be established, meaning that only a noise signal will be measured there. This noise signal is measured at the edges of the one-dimensional magnetic resonance data set and forms a good starting point for determining the outer boundary of a part of the body. For this however the average level of the noise signal, i.e. the average noise value, should be known, which can be determined by a dedicated measurement for example if there is no patient in the combined MR-PET device, but also even when areas are known in which the presence of a part of the body can be excluded, can be determined directly from the one-dimensional magnetic resonance data set. Naturally the same sequence should be used for additional measurement of the average noise value with which the one-dimensional magnetic resonance data set will also be recorded. Starting from the edge of the one-dimensional magnetic resonance data set it can now be checked for example step-by-step whether the measurement signal of the magnetic resonance data set exceeds a first threshold value, with five times the average noise value having been shown to be especially suitable for this measurement. The position at which the exceeding of the first threshold value curve represents an outer limit of a part of the body.

Preferably at least two boundaries can be determined by a step-by-step observation of the measurement signals of the magnetic resonance data set, starting at noise signal areas lying at the edges of the magnetic resonance data set. This has already been discussed in relation to the embodiment using a first threshold value, however the two-sided method described here is advantageous in the respect that—as already mentioned—very low measurement signals can occur in the torso through phase dispersion which can result in incorrect determinations of boundaries. Therefore the method can operate from both sides from outside to inside until the torso is reached, in which case it is known for example that boundaries of the arms and the torso must be determined. The approach from two edges means that a use of the central area is thus avoided.

In concrete terms for the case of a number of parts of the body following on from each other in the imaging direction, especially arms and torso, there can be provision for adjoining boundaries of parts of the body to be determined by a step-by-step observation of the measurement signals of the magnetic resonance data set so that initially a local maximum and its maximum signal value lying inside a part of the body will be determined, after which, in the direction of observation and based on a drop in the measurement signal to a second threshold value determined by the maximum signal value, especially 80% of the maximum signal value, a minimum area with a minimal signal value is determined according to which in the direction of observation a rise of the measurement signal again occurs to at least a third threshold value determined by the minimum signal value, especially 120% of the minimum signal value, so that the boundaries of the minimum area in which the measurement signal exceeds the third threshold value are determined as adjacent boundaries of adjacent body parts.

For example in at least one embodiment of this method of operation, as described above, an outer boundary of a part of the body, for example of an arm, can first be determined by the jump starting from the average noise value. Then it is known where a part of the body begins and a prominent maximum which is especially not influenced by usual measurement fluctuations can be determined. If this is known first then afterwards a minimum area is searched for, likewise uninfluenced by fluctuations as far as possible, of which the minimum value is set sufficiently lower. If such a minimum area is found it can be assumed that it is located between two adjacent body parts. A threshold value method can then be used again to establish where the boundaries of this minimum area which represent boundaries of the adjacent parts of the body, are located. It has especially been shown during the development of the present invention that in most cases the measurement signal drops back between the torso and the arms again approximately to the level of the average noise value, while a characteristic high increase was observed in the area of the outer boundary of the torso. The threshold values should in such cases be selected so that for example a minimum area located centrally in a part of the body as a result of the bone scarcely delivering a signal is not detected as an area between two parts of the body.

On the basis of the information obtained about the boundary of parts of the body, in the final analysis their position and extent, as already discussed, an adaptation and/or determination of at least one part of the attenuation map can be undertaken. Thus there can usefully be provision for a geometrical adaptation, especially positioning, of a least one part of the attenuation map and/or a determination of a least one part of the attenuation map to be undertaken by firming up at a body part-specific model on the basis of the boundaries.

If for example the parts of the body mainly involve the arms, then it should be stated that these are basically very simple in their internal structure and, by contrast with the torso which has a complex structure and is moved from time to time by a cyclic movement, they do not move. Then for example the part of the attenuation map relating to the arms can be easily adapted. Thus an actually measured attenuation map of the arms can be correctly repositioned with reference to the boundaries, i.e. geometrically adapted. However it is also conceivable equally well for example, if the attenuation map of the torso is determined from magnetic resonance images, to enhance the position of a body type-specific model geometrically, for example a generally-usable model of the distribution of the attenuation coefficients in the arm with its quite simple structure as already discussed. Here too this model can be suitably positioned and/or scaled.

Furthermore there can be provision during the determination and/or adaptation, especially scaling, for at least one part of the attenuation map to take account of the measurement signals of the magnetic resonance data set between two boundaries. If in addition, as already discussed, diagnostic statements or similar are not possible in the area for example of the arms or other remote body parts, it is entirely possible—for example in the already mentioned weighting through the corresponding sequence—to also derive statements about the tissue distribution in a part of the body from the one-dimensional magnetic resonance data set. For example a distinction can be made through the appropriate sequences for an arm between tissue which tends to hold fat (fatty tissue) and tissue which tends to hold water (muscle tissue). It is known that bones tend to deliver little signal.

In at least one embodiment of the present case of a combined MR-PET device in particular in many cases additional information can be obtained from a non-corrected PET data set. Thus there can be provision for body surface information from a non-corrected Positron Emission Tomography image data set to be determined and for the boundaries to be taken into account in the determination. This utilizes the fact that a few PET tracers used, especially the frequently used FDG (fluordesoxyglucose) accumulate in the skin, and thus with specific PET image data sets can deliver very clear information about the position of the skin and thus of the surface of the body, which can be noted in respect of the boundaries. This is unsuitable as a stand-alone method however because of the plurality of possible PET examinations, since the information is only available in specific cases. For example no skin surface is able to be detected with functional PET. The body surface information additionally obtained can for example be used to extrapolate boundaries obtained from a one-dimensional magnetic resonance data set into other areas.

BRIEF DESCRIPTION OF THE DRAWINGS

Further advantages and details of the present invention emerge from the example embodiment described below as well as with reference to the drawing. The figures show.

DETAILED DESCRIPTION OF THE EXAMPLE EMBODIMENTS

Figure 1:
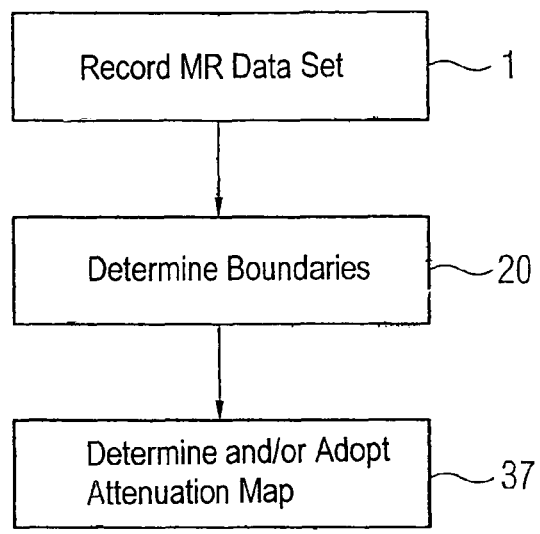
FIG. 1 a flowchart of the inventive method.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 5:
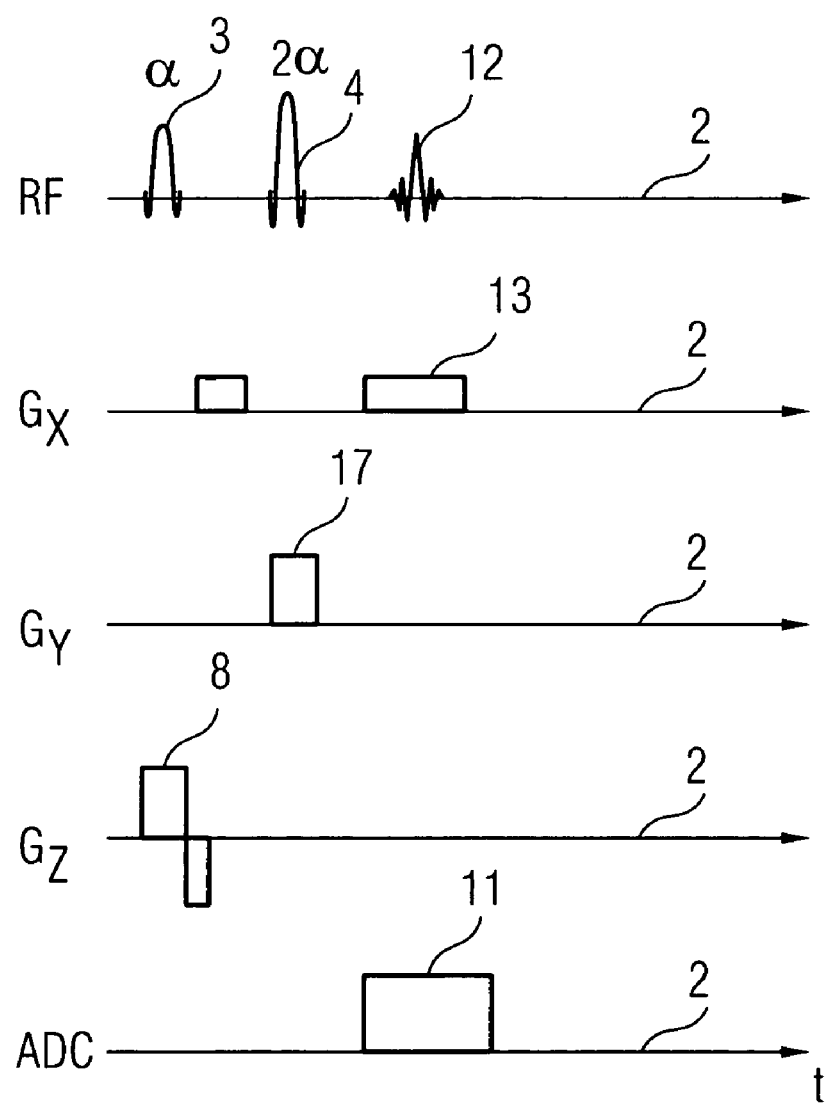

FIG. 1 shows a flowchart of an embodiment of an inventive method. In a step 1 at least one one-dimensional magnetic resonance data set is first recorded. While the present exemplary embodiments are directed, without restricting the generality, to the case in which the boundaries of the arms and the torso of a patient are detected, it is especially advantageous to record at least three one-dimensional magnetic resonance data sets which show the position of the torso and the arms in three different transversal planes. To enable such a one-dimensional magnetic resonance data set to be recorded, a corresponding sequence is required. Examples of usable sequences are shown in FIGS. 2 and 5.

In these figures $G_x$, $G_y$ designate RF excitation or receive pulses respectively of a high-frequency coil of the combined MR-PET device and $G_z$ designates gradient pulses of the gradient coils of the MR-PET device and ADC the read-out activity of read-out electronics of the MR-PET device. The axes 2 each indicate the timing curve. It is evident that the sequence involved is a spin-echo sequence with an excitation pulse 3 and a refocusing pulse 4. The sequence depicted in FIG. 2 will now first be explained in greater detail, with FIGS. 3 and 4 explaining the geometry of the measurement more closely.

Figure 3:
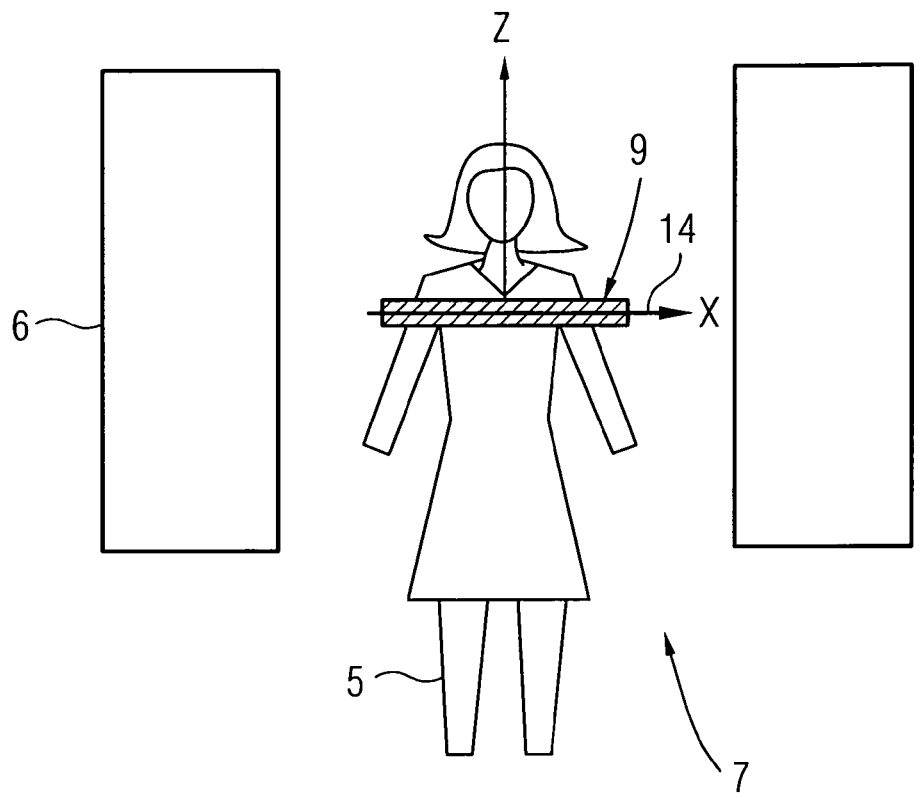

FIG. 3 shows a sketch of a patient 5 in the MR-PET device 6 with patient support 7 only indicated in this diagram for carrying out an embodiment of the inventive method. The caudal-cranial direction is shown in this figure by the letter Z, the left-to-right direction by the letter X and the anterior-posterior direction (cf. FIG. 4) by the letter Y.

Figure 2:
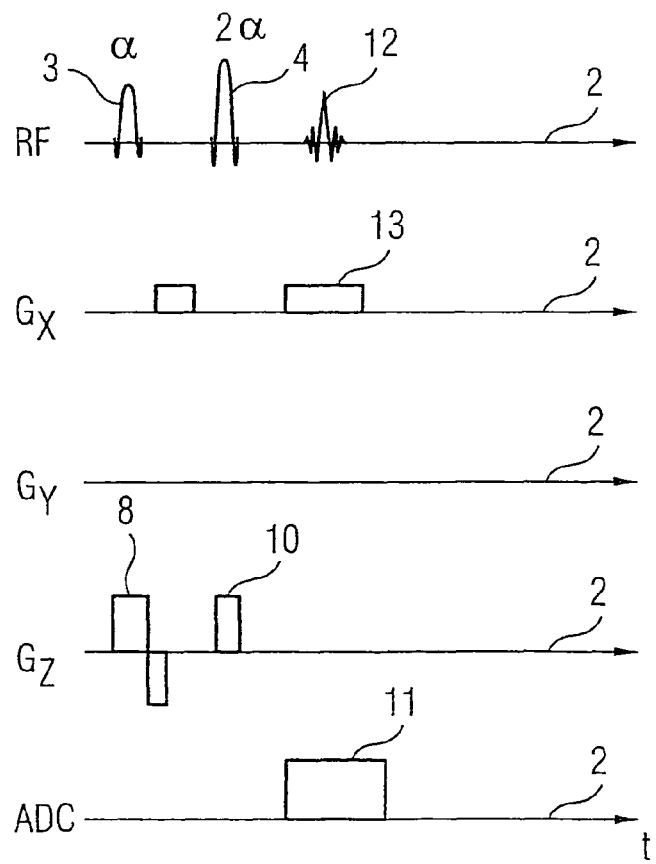
FIG. 2 a possible magnetic resonance sequence for recording a one-dimensional magnetic resonance data set, FIG. 3 a basic diagram of a patient in a combined MR-PET device to explain the geometry, FIG. 4 the projection of the anatomy of a patient in a one-dimensional image data set, FIG. 5 a second example for a magnetic resonance sequence for recording a one-dimensional magnetic resonance data set, FIG. 6 a possible measurement signal curve of a one-dimensional magnetic-resonance data set, and FIG. 7 a basic sketch for a possible model of an arm.

Initially, by switching a layer selection gradient 8 simultaneously with the excitation pulse 3, a layer 9 in the Z direction is selected by the sequence shown in FIG. 2, said layer running in this figure through the shoulders of the patient 5. A further layer selection gradient 10 in the Z direction is switched with the refocusing pulse 4.

It is evident however in the read-out interval 11 that only one local encoding gradient 13 is switched in the X direction to accept the measurement signal 12. The Y direction, i.e. the anterior-posterior direction, is not locally encoded, so that along the acceptance direction 14 lying along the left-to-right direction X the measurement signals of the entire layer 9 are accepted in the anterior-posterior direction. This is explained in more detail by FIG. 4. Obviously the anatomy 15 of the patient 5 which lies in the layer 9 will be projected onto the recording direction 14 lying in the X direction, so that a projection 16 is produced.

Figure 4:
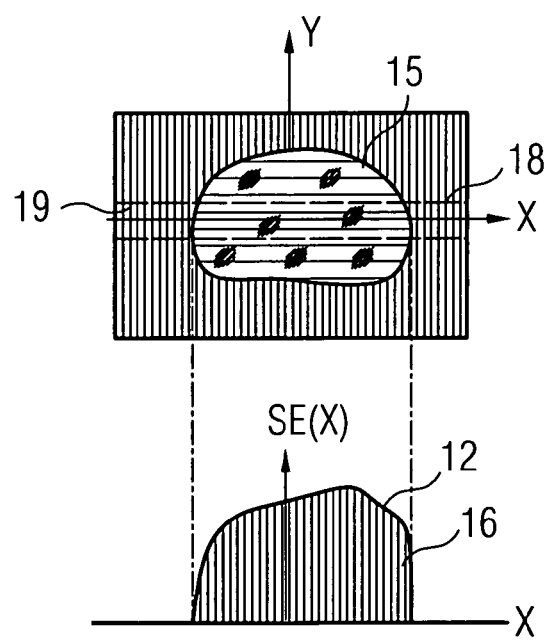

In this case FIG. 4 shows an idealized state however in which no phase dispersion in the anterior-posterior direction occurs in the layer 9. This is however frequently not the case in reality, so that extinctions instead of summations can result during the projection. The second sequence shown in FIG. 5 counteracts this. It can be seen here that instead of the layer selection gradient 10 in the Z direction a layer selection gradient in the Y direction is set synchronously with the refocusing pulse 4. This means that, as well as the selection of the transversal layer 9, this is further restricted in the anterior-posterior direction with the refocusing pulse 4, as is shown for example by the dashed lines 18 in FIG. 4. In this way phase dispersion effects are countered and eventually an essentially rectangular area 19 is measured out.

It should also be noted at this point that in a further embodiment of the sequences from FIG. 2 and FIG. 5, specific weightings can also be provided which either especially accentuate the boundaries of body parts, but also—especially with a number of images in the same layer 9 or in the same area 19—show specific types of tissue or characteristics accentuated, for example by a T1- or T2-weighting or by a fat or water-suppressing measurement. For example it can be established in this way whether more watery (muscle) or more fatty tissue has contributed in the projection. This topic will be returned to later in relation to the adaptation of an attenuation map.

Figure 6:
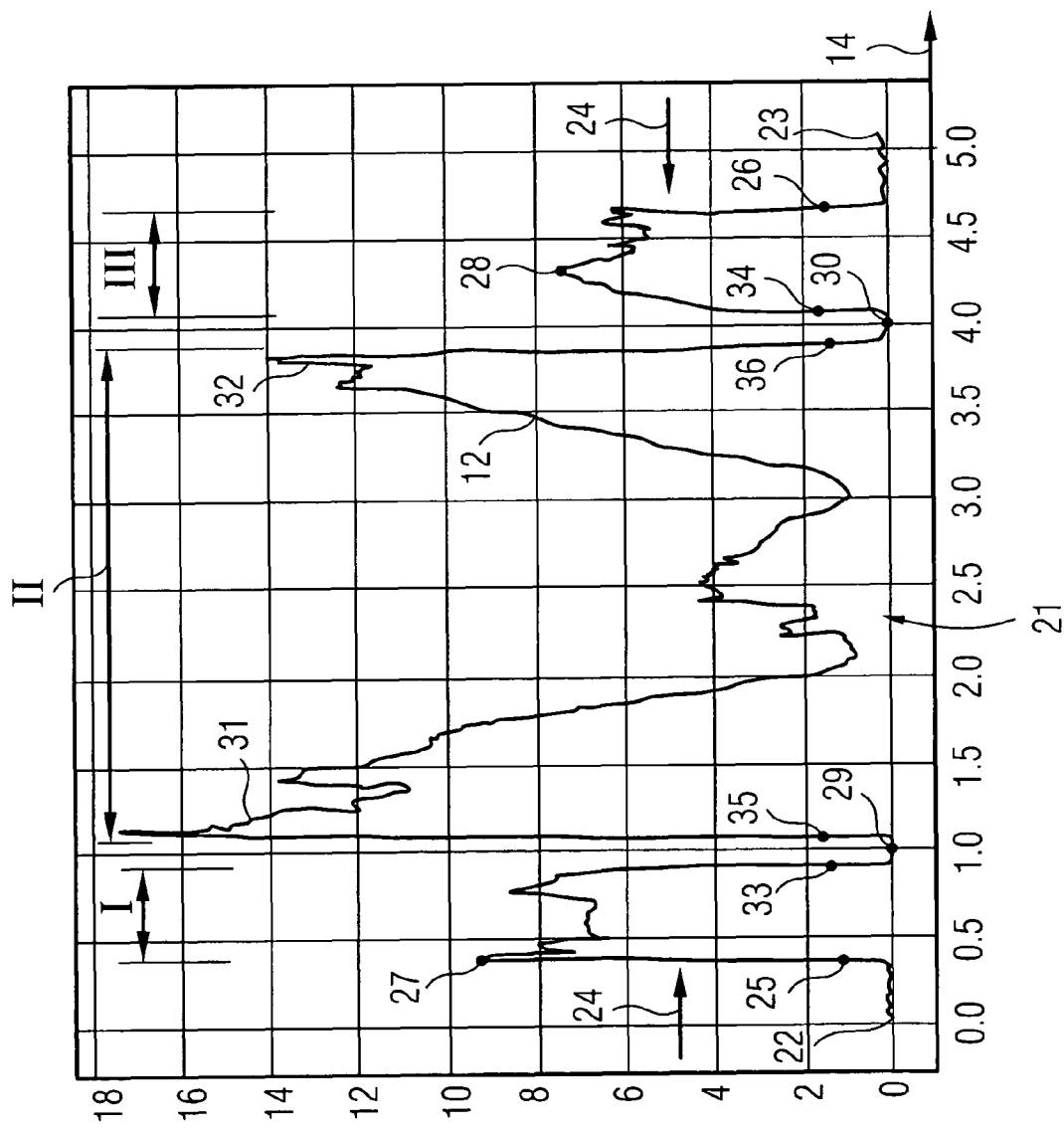

In a step 20 (FIG. 1) the magnetic resonance data set or data sets recorded will now be evaluated so that the boundaries of body parts can be determined from them. This is to be explained by way of an example for a one-dimensional magnetic resonance data set running in the left-to-right direction through the arms and the torso which was imaged with the sequence shown in FIG. 2. Its measurement signal 12 is shown as an example against the position in the imaging direction 14 in FIG. 6. It should be noted in advance that the signal return in the central area 21 is conditional on phase dispersion effects. By qualitative observation of the course of the measurement signal 12 it is already evident that the arms are located in the areas I and III, the torso in area II.

The boundaries of the areas I-II and thus the boundaries of the corresponding parts of the body are now to be determined automatically. To this end there is provision in the inventive method for the measurement signal 12 to be deserved from both edges 22 and 23 of the one-dimensional magnetic resonance data set step-by-step inwards, cf. arrows 24. Since the location is outside the body it is evident that initially only a very low noise signal is measured. The level of this noise signal is described by an average noise value which can be determined from the observed one-dimensional magnetic resonance data set itself or by a separate measurement with the same sequence when the patient is not present. It is now checked step-by-step whether the measurement signal 12 exceeds 5 times this average noise value as first threshold value. This is the case at points 25 and 26. This position is stored and corresponds to the outer boundary of the arms.

In a further step the maximum 27 or 28 respectively occurring in the arm area I or III respectively is determined before the measurement signal 12 falls back again, especially a fall of the measurement signal at least to 80% of the respective maximum signal value 27 or 28 respectively (second threshold value) occurs. The minimum area lying between the area I and II or III and II respectively is now found. This is characterized by a minimum signal value 29 or 30 respectively.

Starting from the respective minimum area, its boundaries are now determined by the measurement signal 12 exceeding a third threshold value derived from the respective minimum signal value. In the present example the third threshold value itself is determined as non-linearly dependent on the minimum signal value. Since the minimum signal value 29 or 30 respectively presently lies in the area of the average noise value, here too an exceeding of 5 times the minimum signal value 29, 30 is required as the third threshold value, which can be easily determined because of the characteristic peaks 31, 32 at the edge of the torso. Points 33-36 are produced as further delimitations, with the points 33 and 34 adjoining the minimum area at the edges 22 and 23 representing the inner boundaries of the arms, while the points 35 and 36 represent the outer boundaries of the torso. It should be noted at this point that—in addition also dependent on the imaging sequence used and any weighting undertaken—the first through third threshold value could naturally also be other than those given here.

In this way the boundaries of the arms and of the torso have been determined from the one-dimensional data set.

Further information can also be obtained from the magnetic resonance data set, for example if a corresponding weighting was undertaken by the sequence. Fat-rich or fat-poor areas and the like can be detected, other additional information can be recorded by comparison of magnetic resonance data sets recorded with different sequences along the same imaging direction 14 as part of the evaluation in step 2. By skillful selection of the sequences and the recording parameters water-dominated (i.e. dominated by muscle mass) fat-dominated and bone-dominated areas within the arms can be determined. Basically it would even be conceivable to use such information on a stand-alone basis to determine a part of the attenuation map.

In a step 37 an at least part determination and/or adaptation of an attenuation map used for attenuation correction of Positron Emission Tomography image data sets is now finally undertaken. Since many options are conceivable, only a few variants will be discussed here with reference to the example of determining the position of the arms.

Figure 7:
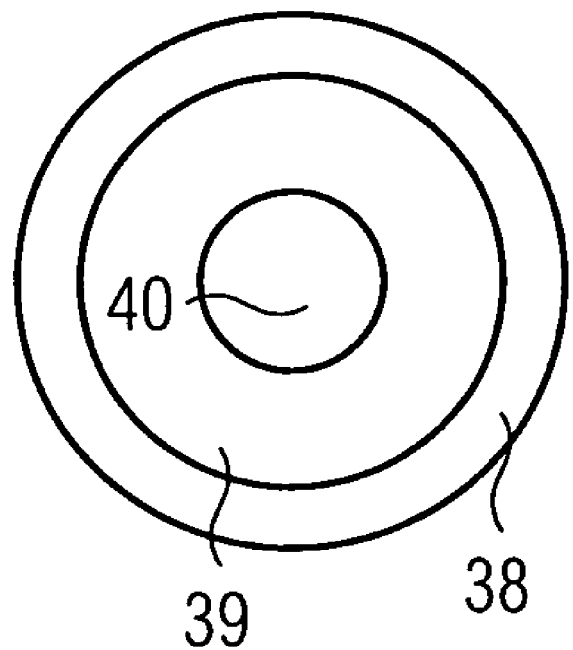

For this it will now be assumed that the attenuation map for the torso is already known, for example already determined by previous dedicated magnetic resonance imaging. Then it is possible to determine the already available attenuation map easily for the arms, by using a simple model for the attenuation in the arms as a basis. Such a simple model is given as an example in FIG. 7. In this figure the arm is essentially assumed to be round, with fat dominating in an outer layer 38, muscle tissue 39 in a central layer 39 and the bone in an inner layer 40. Because of the boundaries of the arm are known from step 20 this model can now be adapted geometrically, meaning suitably laid in its position and scaled with the extent of the arm. The attenuation map can then be supplemented by the component thus determined. If, as already explained, additional information has already been determined for the measurement signal 12 of one or more magnetic resonance data sets, these can also be taken into account for further adaptation of the model.

In another variant there can be provision for example for an attenuation map of a patient which may have already been recorded during an earlier examination to be available, from CT images for example. By determining the boundaries of the arms and the torso it is now known however how the patient is actually positioned in the combined MR-PET device. In this case a geometrical adaptation, for example by repositioning specific portions of the attenuation map, is also possible here.

It should be noted that for example, if magnetic resonance data sets of the arms and the torso are only recorded in three different transversal layers, the course of the arms and if necessary the torso can also be determined between or beyond these transversal layers by interpolation or extrapolation. It is especially advantageous however if additional body surface information can be obtained from an uncorrected PET image data set. This is the case for example if FDG is used in a non-functional PET image as the PET tracer, since FDG in high concentration accumulates in the skin of the patient and this can thus easily be determined as the body surface from the PET image data set. This additional body surface information can advantageously be used for interpolation or extrapolation of the boundaries outside or between the one-dimensional magnetic resonance data sets.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for at least one of at least partly determining and adapting an attenuation map used for attenuation correction of Positron Emission Tomography image data sets in a combined Magnetic Resonance-Positron Emission Tomography device, the method comprising:
   recording at least one one-dimensional magnetic resonance data set of a patient along an imaging direction;
   determining boundaries, of at least one part of a body of the patient intersected by the imaging direction, from the recorded at least one-dimensional magnetic resonance data set; and
   at least one of at least partly determining and adapting the attenuation map, at least in part, depending on the determined boundaries.

2. The method as claimed in claim 1, wherein, in the recording of the magnetic resonance data set, a sequence with local encoding is used during recording in just the imaging direction.

3. The method as claimed in claim 1, wherein, in the recording of the magnetic resonance data set, a spin echo sequence is used.

4. The method as claimed in claim 1, wherein, in the recording of the magnetic resonance data set, a layer selection is undertaken in two directions perpendicular to each other and to the imaging direction, so that an essentially rectangular area is measured out in one dimension.

5. The method as claimed in claim 4, wherein a sequence with two excitation pulses is used, in which, in each case, one layer selection gradient is switched in two directions perpendicular to each other and to the imaging direction.

6. The method as claimed in claim 4, wherein, when a spin echo sequence is used, a layer selection gradient is switched for a refocusing pulse which is perpendicular to the direction selected for a layer selection gradient for an excitation pulse and to the imaging direction.

7. The method as claimed in claim 1, wherein a sequence highlighting at least one type of tissue is used in the recording of the magnetic resonance tissue type, especially a T1 or T2-weighted sequence and/or a water or fat-suppressing sequence.

8. The method as claimed in claim 1, wherein between 2 and 6 different magnetic resonance data sets are recorded.

9. The method as claimed in claim 1, wherein the imaging direction is a right-to-left direction and a layer selection is undertaken at least in the cranial-caudal direction.

10. The method as claimed in claim 1, wherein the imaging direction or an imaging direction intersects the arms and the torso of the patient.

11. The method as claimed in claim 1, wherein an average noise value of a noise signal is determined from the magnetic resonance data set or from a further magnetic resonance data set, with the exceeding of a first threshold value dependent on the average noise value, by the measurement signal starting from a noise signal range, serving to determine a boundary.

12. The method as claimed in claim 1, wherein at least two boundaries are determined by step-by-step observation of the measurement signals of the magnetic resonance data set starting from noise signal areas lying at the edges of the magnetic resonance data set.

13. The method as claimed in claim 1, wherein, for a number of parts of the body following each other in the imaging direction, adjacent boundaries of body parts are determined by step-by-step observation of the measurement signals of the magnetic resonance data set such that a local maximum and its maximum signal value lying within a part of the body will be determined, whereupon a minimum area with a minimum signal value is determined in the direction of observation based on a drop in the measurement signal to at least one second threshold value determined by the maximum signal value, wherein after the minimum signal value an increase in the measurement signal to at least a third threshold value determined by the minimum signal value takes place in the direction of observation, so that the boundaries of the minimum area at which the measurement signal exceeds the third threshold value are determined as adjacent boundaries of adjacent body parts.

14. The method as claimed in claim 1, wherein at least one of a geometrical adaptation of at least one part of the attenuation map and a determination of at least one part of the attenuation map is undertaken by firming up a body-part-specific model on the basis of the boundaries.

15. The method as claimed in claim 1, wherein, in at least one of the determination and adaptation of at least one part of the attenuation map, the measurement signals of the magnetic resonance data set between two boundaries are taken into account.

16. The method as claimed in claim 1, wherein the body surface information is determined from a non-corrected Positron Emission Tomography image data set and is taken into account in determining the boundaries.

17. The method as claimed in claim 16, wherein fluordesoxyglucose (FDG) is used as a Positron Emission Tomography tracer.

18. The method as claimed in claim 7, wherein at least one of a T1 or T2-weighted sequence and a water or fat-suppressing sequence is used in the recording of the magnetic resonance tissue type.

19. A non-transitory computer readable medium including program segments for, when executed on a computer device, causing the computer device to
record at least one one-dimensional magnetic resonance data set of a patient along an imaging direction;
determine boundaries, of at least one part of a body of the patient intersected by the imaging direction, from the recorded at least one-dimensional magnetic resonance data set; and
at least one of at least partly determining and adapting an attenuation map, at least in part, depending on the determined boundaries, the attenuation map used for attenuation correction of Positron Emission Tomography image data sets in a combined Magnetic Resonance-Positron Emission Tomography device.

* * * * *